US009119873B2

(12) United States Patent
Velázquez Miranda

(10) Patent No.: US 9,119,873 B2
(45) Date of Patent: Sep. 1, 2015

(54) USE OF A COMPOSITION COMPRISING A POLY-ORGANOSILOXANE

(71) Applicant: SERVICIO ANDALUZ DE SALUD, Sevilla (ES)

(72) Inventor: Santiago Velázquez Miranda, Sevilla (ES)

(73) Assignee: SERVICIO ANDALUZ DE SALUD, Sevilla (ES)

( * ) Notice: Subject to any disclaimer, the term of this patent is extended or adjusted under 35 U.S.C. 154(b) by 0 days.

(21) Appl. No.: 14/361,164

(22) PCT Filed: Oct. 11, 2012

(86) PCT No.: PCT/EP2012/070167
§ 371 (c)(1),
(2) Date: May 28, 2014

(87) PCT Pub. No.: WO2013/053830
PCT Pub. Date: Apr. 18, 2013

(65) Prior Publication Data
US 2015/0087880 A1    Mar. 26, 2015

(30) Foreign Application Priority Data
Oct. 11, 2011    (ES) .................................. 201131637

(51) Int. Cl.
| | |
|---|---|
| A61K 41/00 | (2006.01) |
| A61L 31/06 | (2006.01) |
| A61N 5/10 | (2006.01) |
| A61K 31/80 | (2006.01) |

(52) U.S. Cl.
CPC .............. *A61K 41/0038* (2013.01); *A61K 31/80* (2013.01); *A61L 31/06* (2013.01); *A61N 5/10* (2013.01); *A61N 5/103* (2013.01); *A61N 2005/1087* (2013.01); *A61N 2005/1096* (2013.01); *A61N 2005/1097* (2013.01)

(58) Field of Classification Search
USPC ........................................... 250/492.1, 492.3
See application file for complete search history.

(56) References Cited

U.S. PATENT DOCUMENTS

| | | | |
|---|---|---|---|
| 6,231,858 | B1 | 5/2001 | Izeki et al. |
| 8,219,354 | B2 | 7/2012 | Campana et al. |
| 2008/0123810 | A1 | 5/2008 | Kirkpatrick et al. |
| 2011/0117008 | A1* | 5/2011 | Shastri et al. ................ 424/1.11 |

FOREIGN PATENT DOCUMENTS

| | | |
|---|---|---|
| JP | H11221293 A | 8/1999 |
| WO | 2008054823 A2 | 5/2008 |
| WO | 2008119905 A1 | 10/2008 |

OTHER PUBLICATIONS

International Search Report dated Feb. 7, 2013.
Wang, Russell R., et al.; "A direct method for fabricating tongue-shielding stent," The Journal of Prosthetic Dentistry, 1995, pp. 171-173, vol. 74.

(Continued)

*Primary Examiner* — Kiet T Nguyen
(74) *Attorney, Agent, or Firm* — McCarter & English, LLP; Danielle L. Herritt

(57) ABSTRACT

A composition based on a poly-organosiloxane which is suitable for its use as a bolus in radiotherapy treatments. Other possible uses of this composition are the production of an immobilizing mask for radio surgery or cranial stereotaxy treatments and the production of an intraoral depressor.

16 Claims, 4 Drawing Sheets

(56) References Cited

OTHER PUBLICATIONS

Farahani, M., et al.; "New method for shielding electron beams used for head and neck cancer treatment," Medical Physics, 1993, pp. 1237-1241, vol. 20.

Farahani, M., et al.; "Shielding Small-Field High-Energy Electron Beams in Cancer Treatment," Radiation Physics & Chemistry, 1994, pp. 357-360, vol. 43.

Havelka, Carole, et al.; "Custom oral appliance for noninvasive immobilization during stereotactic radiotherapy," Pediactric Dentistry, 1995, pp. 212-215, vol. 17.

Farahani, M., et al.; "Metal-polysiloxane shields for radiation therapy of maxillo-facial tumors," Medical Physics, 1991, pp. 273-278, vol. 18.

\* cited by examiner

USE OF A COMPOSITION COMPRISING A POLY-ORGANOSILOXANE

CROSS-REFERENCE TO RELATED APPLICATIONS

This application is filed under the provisions of 35 U.S.C. §371 and claims the priority of International Patent Application No. PCT/EP2012/070167 filed on 11 Oct. 2012 entitled "USE OF A COMPOSITION COMPRISING A POLY-ORGANOSILOXANE" in the name of Santiago VELÁZQUEZ MIRANDA, which claims priority to Spanish Patent Application No. 201131637 filed on Oct. 11, 2011 both of which are hereby incorporated by reference herein in their entirety.

FIELD OF THE INVENTION

The object of the present invention belongs to the field of medicine; the invention is related with a composition based on a poly-organosiloxane which is suitable for its use as a bolus in radiotherapy treatments. Other possible uses of this composition are the production of an immobilizing mask for radio surgery or cranial stereotaxy treatments and the production of an intraoral depressor.

BACKGROUND ART

Radiotherapy is a form of therapy based on the application of radiation to a tumor in order to destroy malignant cells, thereby impeding their growth and reproduction. This therapy may also be applied to normal tissues; however, since tumoral tissues are more sensible to radiation and cannot repair the damage as efficiently as normal tissue, they are destroyed, thus blocking the cellular cycle.

Radiation penetrates a certain distance through the patient's body, in such a way that most of its effect takes place a predetermined distance under the patient's skin depending on the penetrability of each specific radiation type, the effect falling exponentially from that depth. However, sometimes the tumor lies at a depth that is lower than the depth where radiation effect is maximum, such as for example on the patient's skin or very close to it. In those cases, conventional use of radiation hardly has any effect in the tumor area.

In order to solve this drawback, a layer of material having a radiation absorption capability similar to that of the human body may be provided between the radiation source and the skin. If the thickness of the layer is calculated correctly, the radiation acts on the patient's skin. Such an element is known as a "bolus". Some known bolus are disclosed in the following documents:
  U.S. Pat. No. 6,231,858 describes a bolus for radiotherapy made by mixing water with an organic polymer such as gelatin, pectin or various types of gums.
  International application WO 2008/119905 describes a bolus for radiotherapy made of polyurethane.
  International application WO 2008/054823 describes a bolus for radiotherapy made by a mix of an oil gel and a thermoplastic polymer.

Nowadays, it is widely considered that any material used for making a bolus must, in addition to being adaptable to the shape of the patient's skin, have a similar density to that of the human body, that is, to that of water. Thus, if a radiation absorption capability similar to that of the human body is achieved, the bolus will respond to radiation in the same way as the body of the patient.

In connection to this, reference can be made, for example, to the above mentioned prior art U.S. Pat. No. 6,231,858, where column 1, line 57 describes being "equivalent to human body tissue", in the sense, explained some lines below, that "its properties as to radiation absorption and dispersion must be equal to those of human tissue", as the main feature of a bolus. Also page 3, lines 18-19 of prior art international application WO 2008/054823 disclose that a bolus must have "absorption properties similar to those of tissue (or water)". Further, page 9, lines 13-19 of this application disclose the addition of filler material specifically to adjust the bolus density to 1 gr/cm$^3$ (the density of water). The third mentioned international application, WO 2008/119905, emphasizes the fact that the bolus disclosed in this document has a density close to 1 (see page 6, lines 30-32 or page 10, lines 1-8) as an advantageous feature of the invention. Further, page 2, line 28 of the same document discloses that fact that silicone has a density different from 1 as a specific drawback of using silicone.

Furthermore, specifically silicone is considered a material not suitable for making a bolus due to other reasons in addition to its density. For example, column 2, lines 16-29 of international application WO 2008/054823 mentions drawbacks related with cost and cleaning problems in connection with a silicone bolus. Page 6, lines 30-32 of international application WO 2008/119905 also discloses some drawbacks of using silicone for making a bolus, such as the high cost and handling difficulties.

DESCRIPTION OF THE INVENTION

Against all these prejudices in the field, the inventors of the present application have discovered that a composition currently known for making dental molds in the field of dentistry, which is based on a specific type of silicone called poly-organosiloxane having a density different from 1, surprisingly shows unique properties for its use as a bolus in radiotherapy treatments. Specifically, the composition is described in U.S. Pat. No. 6,001,914 as a composition for making dental molds.

Some advantages of this composition when employed for making bolus are the following:
  Since the composition has a higher electronic density than water, specifically about twice the density of water, only half the thickness in comparison with current bolus is required.
  It allows for using photon beams instead of electron beams for superficial treatments. This is very advantageous, since the use of electron beams is now reduced to superficial cancer injuries and has a very high cost. Accelerators supporting clinical electron beams are much more expensive than those supporting photon beams. Quality controls of a radiotherapy service supporting electron beams are much more expensive and inefficient than those needed for photon beams. Dosimetry and calculation entails a higher uncertainty in comparison to photon beams. The treatment itself is longer, since extra time is needed for manually positioning heavy electron collimators. The design of the beams themselves is more complicated with electron beams, since electrons cause great dose gradients in response to small changes in area.
  Since a smaller thickness is required, it is easier to adapt the bolus to the shape of the patient's skin in order to avoid the presence of cavities or bubbles filled with air between bolus and skin. In addition, in case a thermoplastic immobilizer is needed, a thinner bolus is easier to fit under such immobilizer.

It presents a low retraction, allowing an even easier positioning under the skin of the patient without the presence of air cavities or bubbles.

The modeling temperature is low. This is important because many bolus known in the art must be positioned on the patient's skin when still at a high temperature after being produced, often thus causing pain and/or burns.

It presents a high stability for long periods of storage time, even when the temperature is higher than recommended.

Its weight and manufacturing costs are low.

Therefore, a first aspect of the invention refers to a composition comprising a poly-organosiloxane, herein after "composition of the invention", for its use as a medicament, or alternatively, to the use of a composition comprising a poly-organosiloxane for the manufacture of a medicament.

According to a preferred embodiment of the invention, in addition to the poly-organosiloxane, the composition of the invention comprises a crosslinking agent, a platinum catalyst, and a hydrated sodium-aluminum zeolite.

In a further preferred embodiment, the poly-organosiloxane has at least one vinyl group in the end part of the linear molecule.

In one more preferred embodiment, the crosslinking agent contains silicon-hydrogen groups, and more preferably is a poly-hydrogen organosiloxane.

In another preferred embodiment of the invention, the ratio between the zeolite and the platinum catalyst is between 1:0.01 and 1:0.003. In another preferred embodiment of the invention, the zeolite has an average formula of $Na_{12}(AlO_2)_{12}(SiO_2)_{12.27}H_2O$.

More preferably, the composition of the invention further comprises at least an additive. More preferably, the additive is selected from the following group: inhibitors, fillers, release agents, colors, and additives to modify the rheological characteristics, or any combination thereof. Even more preferably, the inhibitors are methyl vinyl cyclotetrasiloxanes. In a further preferred embodiment, the fillers are selected from the group consisting of: quartz, calcium carbonate, silica, talc, or any combination thereof. In a further preferred embodiment, the release agents are paraffin mineral oils. In another preferred embodiment, the rheological modifiers are selected from the group consisting of: quartz, fumed silica, and any combination thereof.

In a preferred embodiment of this aspect of the invention, the medicament is a bolus.

In the present description, the term "bolus" makes reference to a material suitable for being positioned on the skin of a patient and which is capable of partially absorbing radiation employed in radiotherapy treatments with the object of causing its effect to take place on the patient's skin or close thereof. Bolus usually have plastic properties for adapting them to the shape of the patient's skin in the area to be treated with radiotherapy.

The term "radiosurgery" refers to a medical procedure where fine radiation beams, generated in megavoltage units (ciclotron, Gamma Knife, linear accelerator (LINAC)) by means of multiple converging and conformed fields for irradiating high, accurately positioned doses in a specific area or anatomic structure, are administered.

Stereotaxic radiotherapy allows for the administration of the same amount of radiation (or higher) as in conventional radiosurgery, but applied in small distributed doses in daily treatments (fractioned dosage). The fractionation of the dose favors the healing of healthy tissue close to the injury, specially in the case of critic structures such as optic vessels or the cerebral trunk.

Another use of the composition having poly-organosiloxane relates to immobilization devices for radiosurgery or cranial stereotaxy, for fixing the patient's head in a predetermined position in order to arrange reference points in a fixed position with respect to the head during the treatment when images are taken.

Accordingly, in a preferred embodiment of this aspect of the invention, the medicament is a mask for immobilizing the patient in radiosurgery or cranial stereotaxy treatments.

In another preferred embodiment of this aspect of the invention, the medicament is an intraoral depressor or tongue depressor.

The term "medicament" in the context of the present invention refers to a composition comprising a poly-organosiloxane for its use as a bolus in cancer therapy by radiotherapy, for its use as a fractioned stereotaxy immobilizer and as an intraoral depressor.

Another aspect refers to the use of the composition of the invention for the manufacture of a medicament for the treatment of cancer, or alternatively to the composition of the invention for its use in the treatment of cancer. Preferable, cancer is treated by means of radiotherapy, including any radiotherapy medical procedure, such as, for example, without limitation, radiosurgery or stereotaxic radiotherapy. In another preferred embodiment, the radiotherapy, including radiosurgery or cranial stereotaxy treatments, are with photon beams.

Another aspect of the invention refers to the use of a kit for producing a composition of the invention, comprising two separate components wherein:

a first component comprises poly-organosiloxane comprising at least a vinyl group in the end part of the linear molecule and a crosslinking agent; and a second component comprises poly-organosiloxane, a platinum catalyst, and a sodium-aluminum zeolite, for the manufacture of a medicament for the treatment of cancer by radiotherapy.

The present invention also refers to a medical device for radiotherapy comprising the composition of the invention. Then, another aspect of the invention refers to a bolus for use in the treatment of cancer by radiotherapy, comprising the composition of the invention.

Another aspect of the invention refers to a mask for its use in the immobilization of a patient in radiosurgery cranial stereotaxy treatments, comprising the composition of the invention.

Another aspect of the invention refers to an intraoral depressor or tongue depressor, comprising the composition of the invention.

Another aspect of the invention refers to a method for treating cancer patients with radiotherapy comprising use the bolus, the mask or intraoral depressor for directing the radiation to the tumor. In a preferred embodiment the radiotherapy is with photon beam radiation therapy.

Throughout the description and claims, the term "comprising" and all variants thereof do not intend to exclude other technical features, additives, components or steps. For those skilled in the art, the objects, advantages and features of the invention will be derived partly from the description and partly from the practice of the invention. The following examples and figures are provided merely as an illustration, and they are not intended to limit the present invention.

DESCRIPTION OF A PREFERRED EMBODIMENT

Figure 1:
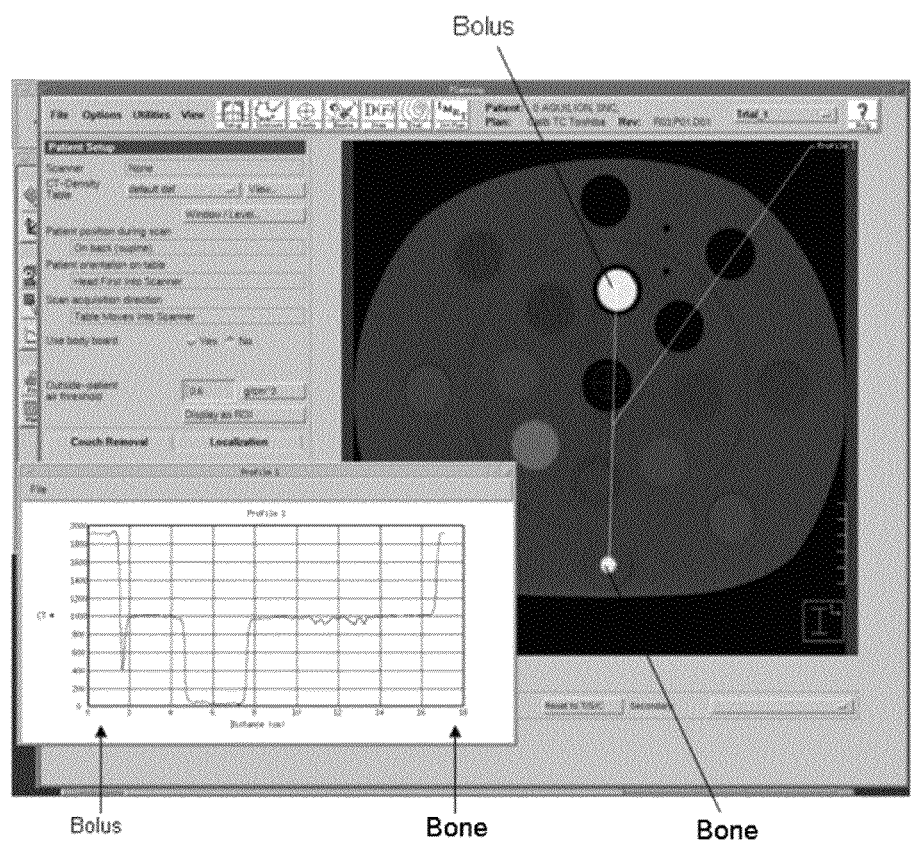
FIG. 1 shows a section made by computed tomography (CT) of a phantom model 062 type "Electron density phantom" of the brand "CIRS: Tissue simulation and phantom technology" on which a sample of a bolus according to the invention and a sample of bone have been provided.

The following paragraphs disclose a preferred embodiment where the composition of the invention is provided by means of two separate components, usually in the form of a paste, which, when mixed, form the composition of the invention and set in some minutes.

a) The first component, known as "base", comprises:
- a poly-organosiloxane having at least a vinyl group in the end part of the linear molecule; and
- a crosslinking agent, preferably a poly-hydrogen organosiloxane.

A filler may be added to this first component, such as for example quartz, calcium carbonate, silica, talc, colors, or any combination thereof.

b) The second component, known as "catalyst", comprises:
- a poly-organosiloxane, preferably having at least a vinyl group in the end part of the linear molecule;
- a platinum catalyst; and
- a stabilizer, preferably a sodium-aluminum zeolite.

Other ingredients may be added in order to complete the composition, such as inhibitors, release agents, additives to modify the rheological characteristics, or any combination thereof.

The preferred inhibitors are methyl vinyl cyclotetrasiloxanes, whilst paraffin mineral oils are advantageously used as release agents.

As regards rheological modifiers, the use of quartz and/or fumed silica is preferred.

As regards the sodium-aluminum zeolite, preferably its average formula is $Na_{12}(AlO_2)_{12}(SiO_2)_{12.27}H_2O$, having the appearance of a water-insoluble white powder. The particles forming it are cube-shaped with rounded corners and edges. The basic elements of the structure of the sodium-aluminum zeolite are shaped like octahedral cubes joined to each other by hexahedrons. The sodium ions, which compensate the excess negative charge, can move freely within the channels of the zeolite.

In the composition of the invention, the zeolite has the primary effect of binding the metal ions, which are harmful for the stability of the platinum catalyst. The exact mechanism of protection towards platinum is currently not clear, but it has been ascertained that the activity of the zeolite preserves the platinum catalyst from the action of any contaminants contained in the composition, thereby prolonging its life. The presence of contaminants is practically inevitable owing to the nature and origin of the components of the compound in which usually mineral fillers are present. It has been found experimentally that optimum results are achieved with a ratio between the zeolite and the platinum catalyst of 1:0.01 and 1:0.003.

Therefore, in the paste hereinbefore referred to as "catalyst", the zeolite preserves the platinum catalyst, so that the composition maintains a constant setting time longer than normal compositions which do not employ zeolite.

It is also possible to use zeolite in the paste described as "base", where it acts as a filler.

Detailed information regarding zeolite may be found in publications of Degusa AG: "Technical bulleting pigments no. 71 Wessalith for detergents", 4th edition: August 1993—Technical information T11160 January 1996. Specific literature on zeolites, also known as molecular sieves, is available in many other publications.

Once the composition has been described with detail, in the following some examples of its use as bolus in radiotherapy are disclosed.

FIG. 1 show a CT section of a phantom model 062 type "Electron density phantom" of the brand CIRS, where the density graph in the foreground shows the density along the white vertical line drawn on the phantom (in the background) downwards from the upper end The graph starts with the measure of the density of a piece of the bolus according to the present invention (positioned in the upper end of the white line) and ends with the density of a bone insert of 800 mg/cc (located in the lower end of the white line). It can be seen that both densities are very similar.

Figure 2:
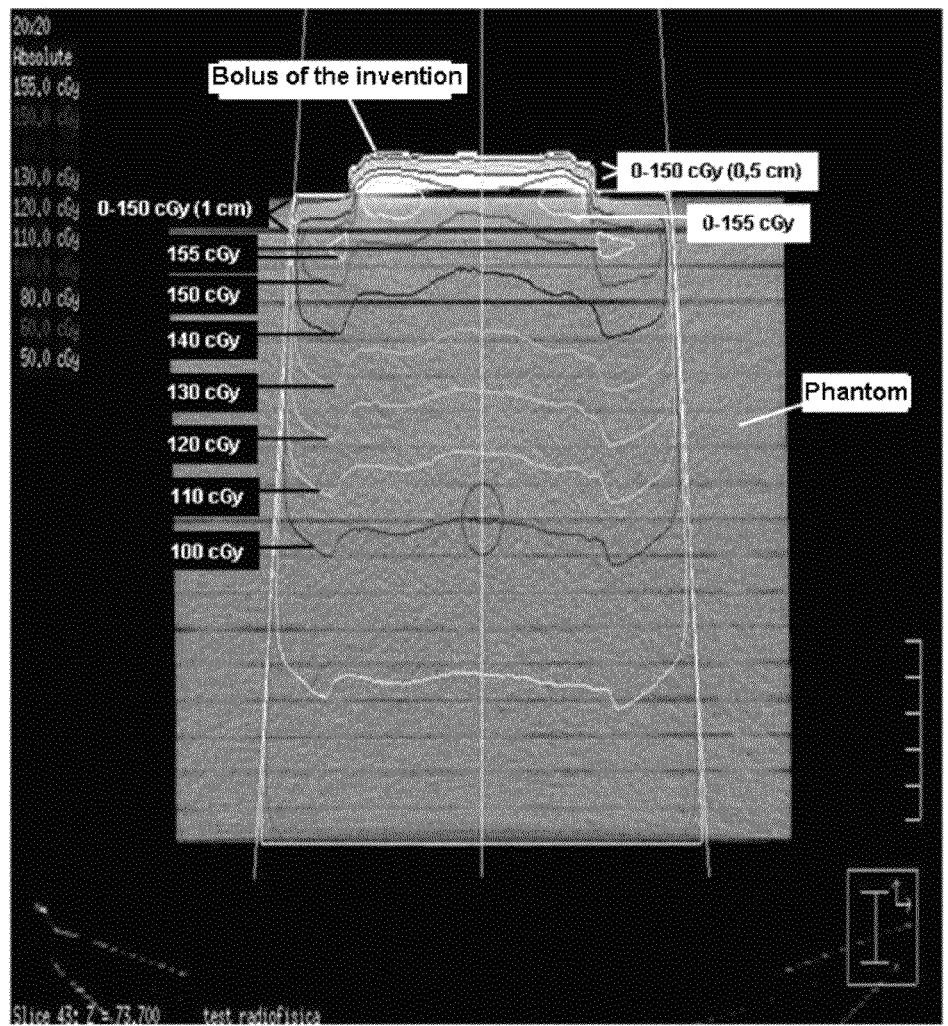
FIG. 2 illustrates the location change in the area corresponding to the maximum radiation received by a phantom having a piece of the bolus of the invention with a thickness of 1 cm thereon when subjected to a 6 MV photon beam.
Figure 3C:
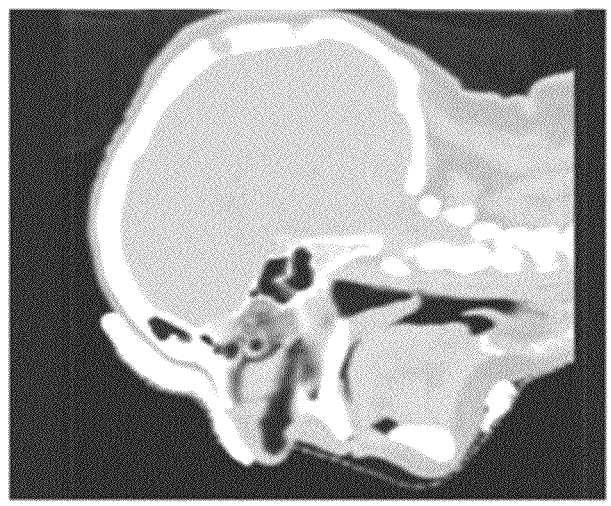
FIGS. 3a, 3b and 3c show respective axial, coronal and sagittal views of the cranium of a patient on which a bolus according to the present invention has been provided.
Figure 3B:
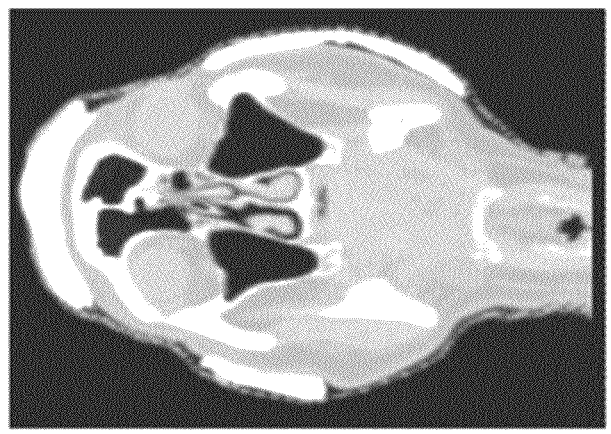
Figure 3A:
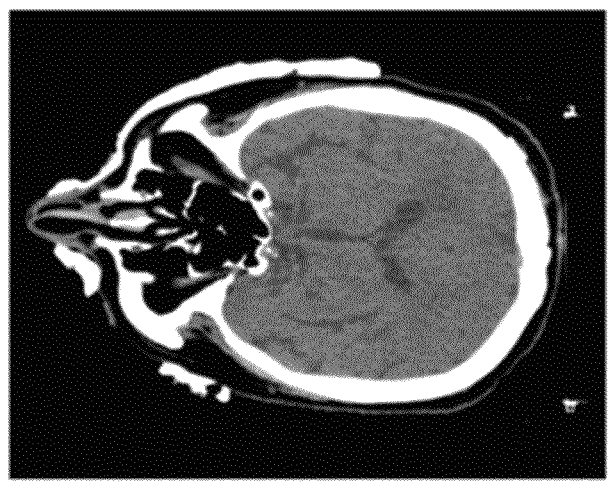

FIG. 2 shows how the distribution of the radiation of a 6 MV photon beam on a phantom changes when a bolus layer of a thickness of 1 cm according to the invention is employed. Note that the original graph presented in the upper left corner a color code corresponding to the different radiation levels. However, since both Spanish and European patent law forbid the use of colors in the figures of a patent application, additional indications disclosing the radiation levels corresponding to each curve have been added.

In the left side of the figure, with white letters on a black background, the radiation levels corresponding to an area of the phantom where the bolus is not affecting are indicated. The distance between the surface of the phantom and the point where a radiation of 150 cGy is found is approximately 1 cm., the maximum of 155 cGy being located at a depth of 1-2 cm; from there, the radiation levels gradually fall as the depth increases.

On the other hand, on the right side of the figure, with black letters on a white background, the radiation levels corresponding to the central zone of the figure where the bolus of the invention is affecting are indicated. In the right side area the depth where 150 cGy are reached is approximately 0.5 cm from the surface of the bolus. The maximum of 155 cGy is located at a depth of approximately 0.5-1 cm, affecting mostly the surface of the phantom located under the bolus. The bolus, therefore, allows for directing the maximum dose of radiation to the surface of the phantom using a conventional photon beam without the need to employ more expensive electron beams.

Figure 4:
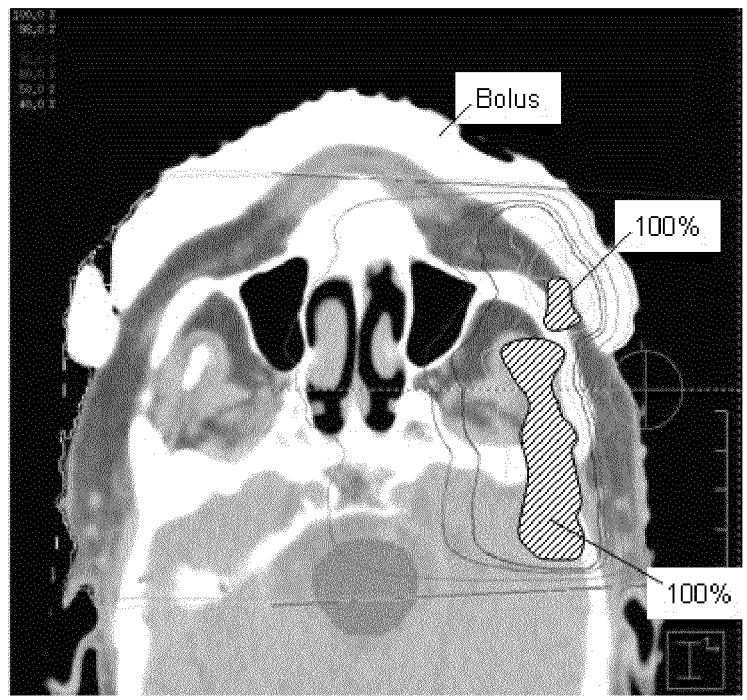
FIG. 4 shows an example of side radiation with a 6 MV photon beam where the differential effect of the bolus can be seen.
Figure 5:
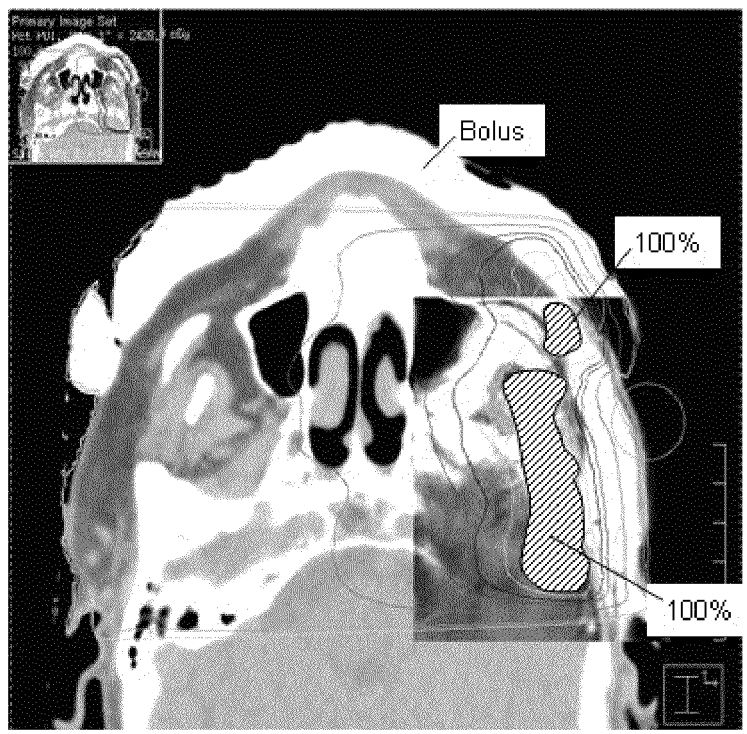
FIG. 5 shows an image captured by computed tomography (CT) fused with magnetic nuclear resonance (MNR) corresponding to FIG. 4.

Therefore, in case the injury to be treated was a skin cancer, a 6 MV photon beam and a bolus of about 1 cm. of thickness could be used in order to make the maximum radiation affect specifically the skin of the patient. This thickness of 1 cm. would be about half the thickness necessary with a conventional bolus having a density equivalent to the density of the tissue of the patient. This is shown in FIGS. 4 and 5 where radiation is shown as a percentage of the maximum dose instead of using cGy. In order to aid in the interpretation of the figure, regions corresponding to 100% of the doses are represented as hatched areas.

Thus, FIG. 4 shows how the presence of the bolus of the invention on the cranium allows for obtaining a region corresponding to 100% of the doses on the surface of the skin, while without the bolus the 100% region is obtained at a depth of 17 mm. FIG. 5 is a fusion of CT and MNR showing how the bolus is virtually invisible in a resonance image, and it does not cause aberrations.

The invention claimed is:

1. A method of using radiotherapy to treat cancer, said method comprising positioning a bolus on skin of a patient in need of treatment thereof, and directing radiation to a tumor to treat said cancer, wherein the bolus comprises a composition comprising a poly-organosiloxane and is capable of partially absorbing radiation.

2. The method of claim 1, wherein the composition further comprises a crosslinking agent, a platinum catalyst and a hydrated sodium-aluminum zeolite.

3. The method of claim 2, wherein the crosslinking agent comprises silicon-hydrogen groups.

4. The method of claim 3, wherein the crosslinking agent is a poly-hydrogen organosiloxane.

5. The method of claim 2, wherein the ratio between the zeolite and the platinum catalyst is between 1:0.01 and 1:0.003.

6. The method of claim 2, wherein the zeolite has an average formula of $Na_{12}(AlO_2)_{12}(SiO_2)_{12.27}H_2O$.

7. The method of claim 2, further comprising at least an additive.

8. The method of claim 7, wherein the additive is selected from the group consisting of inhibitors, fillers, release agents, colors, additives to modify the rheological characteristics, and any combination thereof.

9. The method of claim 8, where in the inhibitors are methyl vinyl cyclotetrasiloxanes.

10. The method of claim 8, wherein the fillers are selected from the group consisting of quartz, calcium carbonate silica, talc, and any combination thereof.

11. The method of claim 8, wherein the release agents are paraffin mineral oils.

12. The method of claim 8, wherein the additives to modify the rheological characteristics are selected from the group consisting of quartz, fumed silica, and any combination thereof.

13. The method of claim 1, wherein the poly-organosiloxane comprises at least a vinyl group in the final part of the linear molecule.

14. The method of claim 1, wherein the radiation comprises photon beams.

15. The method of claim 1, wherein the bolus is in the shape of a mask to immobilize the patient in radiosurgery or cranial stereotaxy treatments.

16. The method of claim 1, wherein the bolus is in the shape of an intraoral depressor.

* * * * *